United States Patent
Nelson et al.

(10) Patent No.: US 6,706,539 B2
(45) Date of Patent: Mar. 16, 2004

(54) ENZYME SUBSTRATE DELIVERY AND PRODUCT REGISTRATION IN ONE STEP ENZYME IMMUNOASSAYS

(75) Inventors: Alan M. Nelson, San Diego, CA (US); Jan W. Pawlak, San Jose, CA (US); Allan D. Pronovost, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 0 days.

(21) Appl. No.: 09/943,031

(22) Filed: Aug. 29, 2001

(65) Prior Publication Data

US 2002/0025541 A1 Feb. 28, 2002

Related U.S. Application Data

(62) Division of application No. 08/977,183, filed on Nov. 24, 1997, now Pat. No. 6,306,642.

(51) Int. Cl.$^7$ .............................................. G01N 33/558
(52) U.S. Cl. ................... 436/514; 436/501; 436/515; 436/518; 436/536; 435/287.1; 435/4; 435/7.1; 435/7.9; 435/18; 435/19; 435/287.2; 435/287.7; 435/287.8; 435/287.9; 435/7.94; 435/7.95; 435/21; 422/55; 422/61; 422/56; 422/57; 422/68.1; 422/70
(58) Field of Search ................ 435/287.1, 4, 7.1, 435/7.9, 18, 19, 287.2, 287.7, 287.8, 287.9, 7.94, 7.95, 21; 436/501, 514, 515, 518, 536; 422/55, 61, 56, 57, 70, 68.1

(56) References Cited

U.S. PATENT DOCUMENTS 3,996,345 A 12/1976 Ullman et al.
4,342,826 A 8/1982 Cole
4,478,944 A 10/1984 Gross et al.
4,632,901 A 12/1986 Valkirs et al.
4,666,830 A 5/1987 Wagner
4,703,017 A 10/1987 Campbell et al.
4,727,019 A 2/1988 Valkirs et al.
4,752,572 A 6/1988 Sundberg et al.
4,828,982 A 5/1989 Wagner
4,857,453 A 8/1989 Ullman et al.
4,868,108 A 9/1989 Bahar et al.
4,904,583 A 2/1990 Mapes et al.
4,912,032 A 3/1990 Hoffman et al.
4,920,046 A 4/1990 Mcfarland et al.

(List continued on next page.)

FOREIGN PATENT DOCUMENTS

| EP | 0 296 724 | 12/1988 |
|---|---|---|
| WO | WO 80/01515 | 7/1980 |
| WO | WO 92/12428 | 7/1992 |
| WO | WO 94/01775 | 1/1994 |
| WO | WO 96/34271 | 10/1996 |
| WO | WO 96/34287 | 10/1996 |
| WO | WO 97/06436 | 2/1997 |

OTHER PUBLICATIONS

Deakin et al., Biochem. J. (1963) 89:296–304.
D'Orazlo et al., Analytical Chemistry (1977) 49(13):2083–2086.

Primary Examiner—Christopher L. Chin
Assistant Examiner—Pensee T. Do
(74) Attorney, Agent, or Firm—Morrison & Foerster LLP

(57) ABSTRACT

One-step enzyme immunoassays in which enzyme-antibody conjugate or label and enzyme substrate are separated until separation of bound and free enzyme conjugate or label is complete. This separation is accomplished by using variable flow paths, immobilization of substrate at the test line, placement of substrate in a sac or association with a particle label, enzyme product chemical capture, delay zone dissolution and protected enzyme substrates.

3 Claims, 6 Drawing Sheets

U.S. PATENT DOCUMENTS

| | | |
|---|---|---|
| 4,966,856 A | 10/1990 | Ito et al. |
| 4,981,786 A | 1/1991 | Dafforn et al. |
| 5,173,406 A | 12/1992 | Hosoda et al. |
| 5,190,864 A | 3/1993 | Giese et al. |
| 5,275,785 A | 1/1994 | May et al. |
| 5,308,775 A | 5/1994 | Donovan et al. |
| 5,354,692 A | 10/1994 | Yang et al. |
| 5,451,504 A | 9/1995 | Fitzpatrick et al. |
| 5,656,448 A | 8/1997 | Kang et al. |
| 5,656,503 A | 8/1997 | May et al. |
| 5,686,315 A | 11/1997 | Pronovost et al. |
| 5,712,172 A | 1/1998 | Huang et al. |
| 5,714,389 A | 2/1998 | Charlton et al. |
| 5,728,587 A | 3/1998 | Kang et al. |
| 5,770,458 A | 6/1998 | Klimov et al. |
| 5,770,460 A | 6/1998 | Pawlak et al. |
| 5,962,336 A | 10/1999 | Sun |
| 5,981,298 A | 11/1999 | Chudzik et al. |
| 5,998,221 A | 12/1999 | Malick et al. |
| 6,001,658 A | 12/1999 | Fredrickson |
| 6,060,582 A | 5/2000 | Hubbell et al. |
| 6,068,859 A | 5/2000 | Curatolo et al. |
| 6,087,185 A | 7/2000 | Lee-Owen et al. |
| 6,121,341 A | 9/2000 | Sawhney et al. |

Where X=(Br, Cl, $OCH_3$, $NO_2$, or $NH_2$) in position ortho or para

| $S_1$ | $Enz_1$ | Product |
|---|---|---|
| ....CH(R₁)-C(=O)-NH-C(=O)-NH₂ peptide | Proteolytic enzymes | urea + amino acids |
| H₂N\C=NH (creatine), H₃C-N, CH₂-COOH | creatine amid inohydnolase (EC 3.5.3.3) | urea + sarcosine |
| HN=C(NH₂)-NH-(CH₂)₃-CH(NH₂)-COOH (arginine) | arginase (EC 3.5.3.1) | urea + ornithine |
FIG. 10
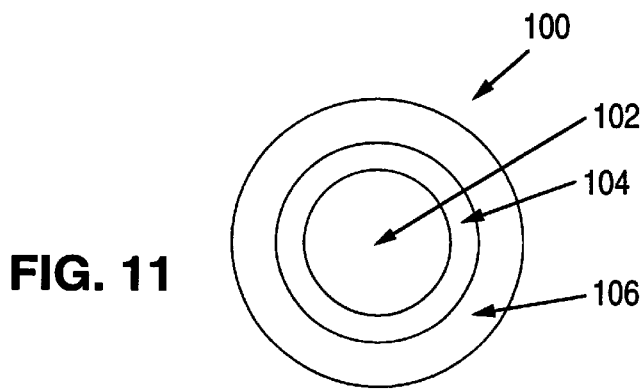
FIG. 11
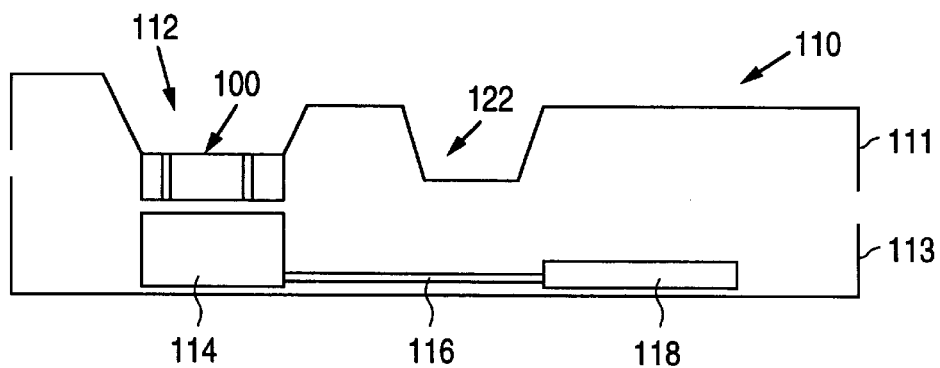
FIG. 12

ENZYME SUBSTRATE DELIVERY AND PRODUCT REGISTRATION IN ONE STEP ENZYME IMMUNOASSAYS

This application is a divisional of prior application Ser. No. 08/977,183, filed on Nov. 24, 1997, now U.S. Pat. No. 6,306,642, from which priority under 35 U.S.C. §120 is claimed.

FIELD OF THE INVENTION

The present invention relates to the detection of analytes in biological fluids. More specifically, the invention relates to enzyme substrate delivery and product registration in one step enzyme immunoassays.

BACKGROUND OF THE INVENTION

Analyte-specific binding assays are important tools for detecting and measuring environmental and biologically relevant compounds, including hormones, metabolites, toxins and pathogen-derived antigens. A convenient version of the binding assay is an immunoassay which can be conducted in a "lateral flow" format.

Devices useful for performing lateral flow assays typically include several "zones" that are defined along a length of a matrix. The matrix defines a flow path and provides fluid connection between the various zones, including a sample receiving zone, a labeling zone for specifically labeling the analyte, and a capture (detection) zone located downstream from the sample receiving zone and the labeling zone. An absorbent zone (sink) typically is located downstream of the capture zone, and provides a means for removing excess sample and unbound label from the matrix.

In some applications the matrix of a lateral flow assay device is a membrane capable of "non-bibulous lateral flow." In these applications liquid flow occurs such that all of the dissolved or dispersed components in the analyte-containing liquid are carried at substantially equal rates and with relatively unimpaired flow laterally through the membrane. This is distinguished from a situation wherein preferential retention of one or more components occurs, for example, in materials capable of adsorbing or imbibing one or more of the components.

A principal advantage of the lateral flow immunoassay is the ease with which the testing procedure is carried out. In this procedure a fluid sample first contacts the matrix following application to the sample receiving zone. Capillary action then draws the liquid sample downstream into a labeling zone that contains a means for indirectly labeling the target analyte. The labeling means generally will be a labeled immunoglobulin, but alternatively may be a non-immunoglobulin labeled compound which specifically binds the target analyte. After flowing through the labeling zone, the sample continues to flow into the capture zone where it contacts an immobilized compound capable of specifically binding the labeled target analyte or the complex formed by the analyte and label. As a specific example, analyte-specific immunoglobulins can be immobilized in the capture zone. Labeled target analytes will bind the immobilized immunoglobulins upon entering the capture zone and will be retained therein. The presence of the labeled analyte in the sample typically will be determined by visual detection of the label within the capture zone. Finally, the procedure is complete when excess sample is taken up by the material of the absorbent zone.

Lateral flow immunoassays typically employ test and procedural control lines in the capture zone. The test line serves to detect an analyte present in a test sample, while the procedural control line conventionally serves to detect a ligand unrelated to the analyte. Rather than being applied in the test sample, the ligand unrelated to the analyte is disposed in the labeling zone of the lateral flow immunoassay device. The test line ordinarily employs specific competitive, sandwich or indirect binding separation principles using a visual label. This requires the use of a labeled detector antibody in the labeling pad of the labeling zone and a capture antibody or ligand immobilized at the capture test line.

The capture zone of lateral flow immunoassay devices may also include a procedure control line useful for indicating that a procedure has been performed. The procedure control line generally is located downstream of the binding compound that is immobilized in the capture zone at the test line where reaction occurs. Retention of label by the procedural control line indicates that liquid sample has flowed through the capture zone and contacted the immobilized target-specific binding substance. The accumulation of visible label may be assessed either visually or by optical detection devices.

Another type of enzyme immunoassay utilizes a flow-through device which is described in U.S. Pat. No. 4,632,901. This device comprises a membrane or filter to which an antibody is bound. An absorbent material in contact with the membrane or filter induces flow therethrough when a fluid sample is added to the membrane or filter. A fluid sample is applied to the membrane and, if the cognate antigen is present, is bound by the antibody. A solution of labeled antibody against the antigen is then added followed by a washing step to remove unbound labeled antibody. The presence of labeled antibody on the membrane after washing indicates the presence of the antigen in the sample being assayed.

In one step enzyme immunoassays (EIAs), whether they be flow-through or lateral flow constructs, there is an inherent limitation to the use of enzyme amplification wherein the enzyme (as either enzyme-antibody conjugate or enzyme-label particulate) must be kept separate from its substrate until separation of bound and free enzyme conjugate or label is complete. The present invention addresses methods for such separation.

SUMMARY OF THE INVENTION

One embodiment of the present invention is an enzyme immunoassay device, comprising a sample pad comprising a slow lane and a fast lane separated by a hydrophobic barrier, wherein the slow lane contains an enzyme substrate and the fast lane contains an enzyme-antibody conjugate having affinity for an analyte; a capture zone in fluid communication with the sample pad, the capture zone having a capture antibody incorporated therein having affinity for said analyte; and an absorbent zone in fluid communication with said capture zone. Preferably, the analyte is a hormone, enzyme, lipoprotein, bacterial antigen, viral antigen, immunoglobulin, lymphokine, cytokine, drug or soluble cancer antigen. Advantageously, the sample pad comprises high density polyethylene.

Another embodiment of the present invention is a flow-through lateral flow enzyme immunoassay device, comprising a disk comprising inner and outer hydrophilic zones separated by a hydrophobic barrier, the inner zone containing an enzyme substrate and having a smaller pore size than the outer zone, the outer zone containing an enzyme-antibody conjugate having affinity for an analyte; a contact pad in fluid communication with the molded disk; a capture zone in fluid communication with the contact pad; and an adsorbent zone in fluid communication with the contact pad.

The present invention also provides a lateral flow enzyme immunoassay device, comprising a sample pad; a label pad in fluid communication with the sample pad, the label pad containing an enzyme-antibody conjugate having affinity for an analyte; a capture zone in fluid communication with the label pad, the capture zone containing a capture antibody having affinity for the analyte; and an enzyme substrate at a test line. In one aspect of this preferred embodiment, the substrate is chemically immobilized at the test line. Alternatively, the substrate is immobilized in a mordant under the test line. Still alternatively, the substrate is immobilized in a mordant dispensed within the test line. Preferably, the capture zone further comprises chemical groups incorporated therein, the chemical groups capable of specifically reacting with the product resulting from enzyme action on the substrate. Advantageously, the chemical groups comprise diazotized amines.

Another embodiment of the invention is a lateral flow enzyme immunoassay device, comprising a sample pad; a label pad in fluid communication with the sample pad, the label pad containing a substrate covalently attached to a particle or imbibed within a sac, wherein the substrate-containing sac or particle is attached to an antibody; a capture zone in fluid communication with the label pad, the capture zone containing an enzyme/mediator for releasing the substrate and a capture antibody at a test line; and an absorbent zone in fluid communication with the capture zone. Preferably, the sac comprises a liposome. Alternatively, the sac comprises an erythrocyte ghost. Advantageously, the particle label comprises polyalkylcyanoacrylate polymer monosized colloids. The enzyme/mediator may immobilized in a mordant within or under the test line, or may be attached to the capture antibody.

The present invention also provides an enzyme immunoassay device, comprising a sample pad comprising a first lane containing a first barrier zone and a second lane containing a second barrier zone, wherein the first lane contains an enzyme-antibody conjugate having affinity for an analyte and said second lane contains an enzyme substrate, wherein the first barrier zone dissolves before said second barrier zone; a capture zone in fluid communication with the sample pad, the capture zone containing a capture antibody incorporated therein having affinity for the analyte; and an absorbent zone in fluid communication with the capture zone. The barrier zones may comprise structural hydrogel, enterosoluble coatings or biodegradable phospholipids.

Still another embodiment of the invention is an enzyme immunoassay device, comprising a sample pad containing a first enzyme and a second enzyme, the second enzyme conjugated to a second antibody having affinity for an analyte; a label pad in fluid communication with the sample pad, the label pad containing a substrate for the first enzyme, wherein the substrate for the first enzyme is converted by the first enzyme to a second substrate for the second enzyme; and a capture zone in fluid communication with the label pad, the capture zone containing a first antibody having affinity for the analyte at a test line, wherein the second substrate is converted by the second antibody to an enzyme product; and an absorbent zone in fluid communication with the capture zone. Preferably, the first enzyme is alkaline phosphatase, esterase, protease, sulfatase, chymotrypsin-like protease, creatine amidinohydrolase or arginase. Advantageously, the second enzyme is β-D-galactosidase, N-acetylglucosaminidase, α-L-arabinofuranosidase, exglucanase, chitobiosidase, α-L-fucosidase, β-D-glycosidase, α-galactosidase, β-glucosidase, glucansucrase, β-D-glucuronidase, α-amylase, α-mannosidase or β-mannosidase. According to another aspect of this preferred embodiment, the analyte is a hormone, enzyme, lipoprotein, bacterial antigen, viral antigen, immunoglobulin, lymphokine, cytokine, drug or soluble cancer antigen.

The present invention also provides a sample receiving layer for use in an enzyme immunoassay device, comprising: a disk comprising inner and outer hydrophilic zones separated by a hydrophobic barrier, the inner zone containing an enzyme substrate and having a smaller pore size than the outer zone, the outer zone containing an enzyme-antibody conjugate having affinity for an analyte.

BRIEF DESCRIPTION OF THE DRAWINGS

FIG. 10 shows "protected" substrates for urease as E1 in E1 Ab conjugates and the resulting products.

FIG. 11 is a top view of a molded disk comprising variable flow paths for use as a top sample receiving layer in the immunoassay device shown in FIG. 12.

FIG. 12 is a cross-sectional view of a flow-through lateral flow enzyme immunoassay device.

DETAILED DESCRIPTION OF THE PREFERRED EMBODIMENTS

Figure 1:
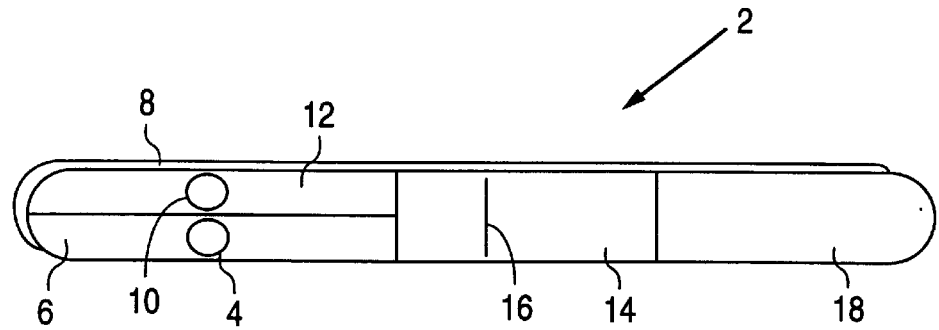
FIG. 1 is a schematic diagram of a lateral flow assay strip containing a variable flow path sample pad.

The present invention provides one step enzyme immunoassay devices and methods in which enzyme and substrate are kept separated until separation of bound from free enzyme conjugate or label is complete. The invented assay devices comprise four distinct zones. The device is designed so that the analyte-containing sample is first applied to a sample receiving zone, then flows through a labeling zone and into a capture zone. The capture zone in turn is in contact with an absorbent zone which provides a means for removing excess liquid sample. In conventional immunoassay devices, the absorbent zone consists of an absorbent such as filter paper or glass fiber filter.

As used herein, the term "pad" refers to the physical material which corresponds to a zone or section of an immunoassay strip. Thus, a sample pad is the material of the sample receiving zone of an immunoassay strip. The labeling pad similarly refers to the material of the labeling zone.

The invention generally concerns one-step lateral flow or flow-through assays which are conducted on supports which may conduct nonbibulous lateral flow of fluids. As defined herein "nonbibulous" lateral flow refers to liquid flow in which all of the dissolved or dispersed components of the liquid which are not permanently entrapped or "filtered out" are carried at substantially equal rates and with relatively unimpaired flow laterally through the membrane or support. This is distinguished from preferential retention of one or more components as would occur, for example, in materials capable of absorbing or "imbibing" one or more components as occurs in chromatographic separations. "Bibulous" materials include untreated forms of paper, nitrocellulose and the like which effect chromatographic separation of components contained in liquids passed therethrough. Bibulous materials can be converted to materials which exhibit nonbibulous flow characteristics by the application of blocking agents. These agents may be detergents or proteins which can obscure the interactive forces that account of the bibulous nature of the supports. Thus, nonbibulous materials include those which are intrinsically capable of conducting nonbibulous flow, such as porous polyethylene sheets or other inert materials or can be comprised of bibulous materials which have been blocked. Preferred blocking agents include bovine serum albumin, either per se or in methylated or succinylated form, whole animal sera, such as horse serum or fetal calf serum, and other blood proteins. Other examples of protein blocking agents include casein and nonfat dry milk. Detergent-based blocking agents can also be used for rendering a bibulous material capable of nonbibulous flow. The types of detergents appropriate for this purpose are selected from nonionic, cationic, anionic and amphoteric forms, and the selection is based on the nature of the membrane that is being blocked.

To convert a bibulous support such as paper or nitrocellulose to a support capable of effecting nonbibulous lateral flow, the original support is treated with a solution of the blocking agent in an effective concentration to dispose of unwanted reactivities at the surface. In general, this treatment is conducted with a blocking solution, such as a protein solution of 1–20 mg/ml protein at approximately room temperature for between several minutes and several hours. The resulting coated material is then permanently adsorbed to the surface by air-drying, lyophilization, or other drying methods. Both the selection and treatment of carrier porous materials used to construct immunoassay strips of the sort described herein depend on the functional role that each zone performs in the assay device.

The sample-receiving zone serves to begin the flow of analyte-containing sample, and typically will be constructed of a material that exhibits low analyte retention. One means for imparting this property involves impregnating the sample receiving zone with a neutral protein-blocking reagent, followed by treatment to immobilize the blocking agent (e.g., lyophilization). An additional advantage of this treatment is increased wetability and wicking action which speeds transfer of the liquid sample into the labeling zone. The sample-receiving zone may also function as a mechanical filter, entrapping any undesirable particulates present in the sample.

The labeling zone contains enzyme-antibody conjugate or particulate moieties which may or may not be visible, which can be detected if accumulated in the capture zone. The visible moieties can be dyes or dyed polymers which are visible when present in sufficient quantity, or can be, and are preferred to be particles such as dyed latex beads, liposomes, or metallic, organic, inorganic or dye solutions, dyed or colored cells or organisms, red blood cells and the like. The enzyme-antibody conjugate or particulate moieties used in the assay provide the means for detection of the nature of and quantity of result, and accordingly, their localization in the capture zone must be a function of the analyte in the sample. In general, this can be accomplished by coupling the enzyme-antibody conjugate or particulate moieties to a ligand which binds specifically to the analyte, or which competes with analyte for a capture reagent in the capture zone. In the first approach, the conjugate or particulate moieties are coupled to a specific binding partner which binds the analyte specifically. For example, if the analyte is an antigen, an antibody specific for this antigen may be used; immunologically reactive fragments of the antibody, such as $F(ab')_2$, Fab or Fab' can also be used. These conjugate or particulate moieties, or "test" moieties, then bind to analyte in the sample as the sample passes through the labeling zone and are carried into the capture zone by the liquid flow. When the complex reaches the capture zone, it is captured by an analyte-specific capture reagent, such as an antibody. Excess liquid sample finally is taken up by the absorbent zone. In the second approach, the conjugate or particulate moieties are coupled to a ligand which is competitive with analyte for a capture reagent in the capture zone, most typically, other molecules of the analyte itself. Both the analyte from the sample and the competitor bound to the conjugate or particulate moieties are then carried into the capture zone. Both analyte and its competitor then react with the capture reagent, which in this instance is also typically specifically reactive with an analyte and its competitor. The unlabeled analyte thus is able to reduce the quantity of competitor-conjugated conjugate or particulate moieties which are retained in the capture zone. This reduction in retention of the conjugate or particulate moieties becomes a measure of the analyte in the sample after enzyme turnover.

The labeling zone of immunoassay devices of the present invention also may include a procedural control which comprises visible moieties that do not contain the specific binding agent or analyte competitor and that are also carried through to a control area of the capture zone by the liquid flow. These visible moieties are coupled to a control reagent which binds to a specific capture partner and can then be captured in a separate procedural control portion of the capture zone to verify that the flow of liquid is as-expected. The visible moieties used in the procedural control may be the same or different color than those used for the test moieties. If different colors are used, ease of reading the results is enhanced.

The experimental results of a procedure conducted using an immunoassay strip are read in the capture zone by noting the presence or absence of a visible signal at the location of the capture zone for the test line. The use of a procedural control region is helpful for indicating the time when test results can be read. Thus, when the expected color appears in the procedural control region, the presence or absence of a color in the test region can be noted. The use of different colors for test and control regions aids in this process.

The use of a matrix which is bibulous inherently, but convertible to a nonbibulous flow characteristic, is particularly useful in the creation of the capture zone. Capture reagents can be applied to the matrix before the application of blocking agents and can be immobilized in situ. At this stage, the bibulous nature of the matrix during the coupling of the capture reagents may be advantageous. However, the blocking/washing treatment which converts the bibulous membrane to nonbibulous support provides unimpaired and speedy flow of all components of the system.

The extremely rapid nature of the assay, which typically yields a result in less than one minute, provides in many instances essentially an instantaneous result as the sample flows due to the nonbibulous nature of the zones and of the short distance the sample must traverse in each zone. Another factor which contributes to the speed of the assay is the absorptive potential of the material used to create the absorbent zone and the use of dessicant as adsorbent.

Miniaturization of the diagnostic device also contributes to the remarkable speed of the assay. Miniaturization permits instantaneous results which are observable as soon as the sample contacts the capture zone and which occur almost immediately or within 60 seconds of the addition of the sample to the sample receiving zone. The speed of appearance and intensity of the positive visible reaction seen depends on the concentration of analyte in the sample. The speed of appearance of the positive visual reaction can be adjusted to provide the optimal visual result with concentrations of analyte of clinical importance and adjusted to suit the timing needs of the end-user.

Suitable analytes detectable by the invented immunoassay devices are any for which a specific binding partner can be found. In general, most analytes of medical and biological significance can find specific binding partners in antibodies prepared against them or fragments of these antibodies. Suitable analytes include soluble analytes such as hormones, enzymes, lipoproteins, bacterial or viral antigens, immunoglobulins, lymphokines, cytokines, drugs, soluble cancer antigens, and the like. Also included as suitable analytes are hormones such as human chorionic gonadotropin (hCG), insulin, glucagon, relaxin, thyrotropin, somatotropin, gonadotropin, follicle-stimulating hormone, gastrin, bradykinin, vasopressin, and various releasing factors. A wide range of antigenic polysaccharides can also be determined such as those from Chlamydia, *Neisseria gonorrheae, Pasteurella pestis, Shigella dysentereae*, and certain fungi such as Mycosporum and Aspergillus. Another major group comprises oligonucleotide sequences which react specifically with other oligonucleotides or protein targets. An extensive list of soluble analytes determinable in the method of the invention is found in U.S. Pat. No. 3,996,345, which is incorporated herein by reference.

The invented immunoassay strips can be disposed within a housing that is both protective and functional. In one preferred embodiment the housing is adapted to have at least one port for receiving a liquid sample and guiding fluid flow of the sample to contact the immunoassay strip at the sample receiving zone. The housing also can have windows which allow a user to view portions of the immunoassay strip, including portions of the capture zone and/or the absorbent zone.

Various enzyme substrate systems can be used in the one-step enzyme immunoassays of the invention. These systems are summarized in Table 1 but not limited thereto.

TABLE 1

| ENZYME | 1) SOLUBLE PRODUCT | 2) INSOLUBLE PRODUCT | pH RANGE |
|---|---|---|---|
| Alkaline Phosphatase | (p-Nitrophenyl phosphate) (p-Aminophyenyl phosphate) Azonaphthol phosphate Naphthyl phosphate | BCIP, 3-IP Azonaphtol phosphate BCIP/tetrazolium salt 3-IP/tetrazolium salt | 9–10.5 |
| Horseradish peroxidase | DAB/MBTY ABTS TMB | 3-AEC 4-Chloronaphthol 4-Chloronaphthol/ MBTH 4-Chloronapthol/ 4-AAP DAB | 4–8 |
| Glucose oxidase | Tetrazolium salt/PMS | Tetrazolium salt/ PMS | 6–8 |
| Diaphorase oxidoreductase | Tetrazolium salt/ NADH (NADPH) | Tetrazolium salt/ PMS | 6–8 |
| Galactosidase | (Azonapthol galactopyranoside) (Aminophenyl galactopyranoside) (Napthyl galactopyranoside) (Nitrophenyl galactopyranoside) | (Indolyl galactopyranoside (Azonaphthol galactopyranoside) | 6–8 |
| Urease | Urea Urea/pH indicator | | 6–8 |
| Glucuronidase | (Azonaphtol glucuronide) (Nitrophenyl glucuronide) Naphthyl glucuronide (Aminophenyl glucuronide) | (Azonaphthol glucuronide) (Indolyl glucuronide) | 6–8 |

1) Product of Reaction of enzyme on substrate is water soluble.
2) Product of Reaction of enzyme on substrate is water insoluble.

Various embodiments of enzyme-substrate delivery and product registration in one-step EIAs are discussed below.

1. Variable Flow Path

A lateral flow EIA device 2 is illustrated in FIG. 1. Enzyme-antibody conjugate (E-Ab) 4 is lyophilized and placed in the fast chromatographic lane 6 of a bi-phase solid support 8. The enzyme substrate 10 is lyophilized and placed in the slow chromatographic lane 12. The "fast" and "slow" lane designations refer to the pore size of the high density polyethylene. The slow lane contains smaller pore sizes than the fast lane. Accordingly, the substrate 10 will move through the sample pad more slowly than E-Ab 4. A volume of sample containing analyte is applied to solid support 8 and contacts both substrate 10 and E-Ab 4 simultaneously. The substrate 8 and E-Ab 4 then flow at variable rates to the nitrocellulose detection zone 14 for sequential conjugate, then substrate, reaction. An immunological separation occurs in the detection zone 14 where analyte-Ab-E complex either binds to the capture antibody at the test line 16 or Ab-E passes unbound to the absorbent zone 18. Upon reaching the immobilized E-Ab, substrate is converted to product which is either insoluble and precipitates at the test line 16, or the soluble product is measured downstream by conventional methods. A specific example of this embodiment is provided in Example 1.

EXAMPLE 1

Substrate and Enzyme-Antibody Conjugate Delivery Using Variable Flow Paths

Molded hydrophilic high density polyethylene (HDPE) macroporous supports such as those custom manufactured by Interflo Technologies (Brooklyn, N.Y.) were used to form the variable flow paths. Two pieces of 2 mm thick hydrophilic HDPE (5 mm×50 cm each) of different pore sizes (5–20 μm and 20–80 μm) were separated by a hydrophobic non-porous material (2 mm×50 cm), aligned along the length parallel to each other on the same plane, then fused together. The resultant "two-lane" strips were cut into 12×20 mm pieces. To each two-lane strip was added a 5 μl aliquot of enzyme-antibody conjugate (3–6 mg/ml), spotted in the center of the fast lane, and 5 μl aliquots of the appropriate enzyme substrate (5–12 mg/ml) supplemented with 10–20% (w/v) of cyclodextrin were spotted in the center of the slow lane. Cyclodextrin was added to increase the viscosity and further retard movement of the substrate through the strip. The prepared materials were lyophilized and assembled as intermediate zones into a lateral "one-step" device. Subsequently, substrate and enzyme-antibody conjugate delivery by use of a variable flow path were studied by applying buffer solutions at different pH.

In a related embodiment, substrate and enzyme-antibody conjugate were delivered using a variable flow path in a flow-through lateral flow device. Referring to FIG. 11, a 20 mm diameter molded disk of HDPE 100 was constructed by fusing a 9 mm diameter inner disk 102 of 5–20 μm pore size hydrophilic HDPE with an outer 2 mm thick O-ring 104 of hydrophobic medium and an outside 9 mm thick O-ring 106 of 20–80 μm hydrophilic HDPE. The inner disk 102 was saturated with the appropriate enzyme substrate solution (0.2–2 mg/ml) containing 5–20% cyclodextrin and the outside ring 106 was saturated with the corresponding enzyme-antibody conjugate (5–25 μg/ml) supplemented with 2–10 mg/ml bovine serum albumin (BSA). The use of any desired diameter disk and O-ring thickness for forming the molded disk 100 is within the scope of the invention. In addition, the use of hydrophilic materials other than HDPE is also contemplated. Such materials include, for example, polypropylene and polyvinylchloride.

The resultant pieces were lyophilized and assembled as a sample receiving top layer of the flow-through device 100 shown in FIG. 12. The device has a top housing 111 and a bottom housing 113. Disk 100, which functions as the label pad, is placed in sample well 112 in contact with absorbent contact pad 114 which is in fluid communication with capture zone 116 and absorbent pad 118. Test line 120 containing a capture antibody is viewable through view window 122.

A fluid sample containing an antigen of interest is applied to the device 110 and, due to the larger pore size of O-ring 106 to which the enzyme-antibody conjugate is applied, the enzyme-antibody-antigen complex moves into the contact pad 114 and capture zone 116 in fluid communication with disk 100 before the enzyme substrate, thus keeping the enzyme and substrate separated until antigen has bound to the antibody at the test line 120. Unbound antigen and reagents flow into the absorbent pad 118.

2. Substrate Delivery Through Immobilization at Test Line

In this lateral flow embodiment, the substrate is immobilized at the test line chemically, in a mordant under the test line (e.g. protein, gel, etc.) or in a mordant dispensed within the test line in the nitrocellulose membrane (e.g. cyclodextrin, polyvinyl acetate, etc.). In a lateral flow assay format, analyte reacts with enzyme-antibody conjugate localized in a label pad, followed by complex formation in the presence of antigen. The complex is captured by the capture antibody immobilized at the test line or proceeds unbound to the absorbent in the absence of analyte. The enzyme product is either insoluble and precipitates on the test line or is soluble and measured downstream.

3. Substrate Delivery Vehicles

Figure 2:
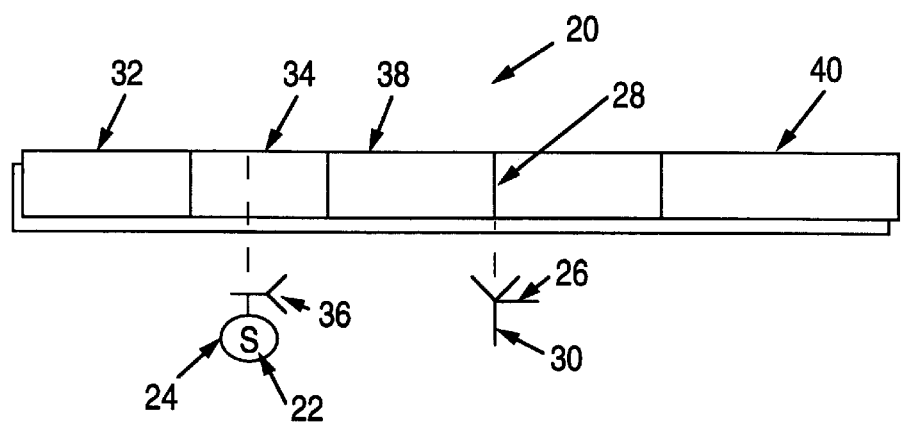
FIG. 2 is a schematic diagram of a lateral flow enzyme immunoassay strip in which the substrate is covalently attached to a particle label or imbibed inside a sac. X=analyte; SP=sample pad; LP=label pad; Nitro= nitrocellulose; S=substrate; Enz/Med=enzyme/mediator.

In one embodiment of this lateral flow EIA device 20 (FIG. 2), the substrate 22 is covalently attached to a particle label, such as a latex particle bound to indoxyl phosphate moieties via primary amine functionalities. Under the influence of alkaline phosphatase (EC 3.1.3.1 from bovine and calf intestinal mucosa), the phosphate ester is cleaved to liberate indol-3-ol which in turn is oxidized by free oxygen in solution to blue indigo dye.

In another preferred embodiment, the substrate is imbibed within a sac 24. One example of an enzymatic substrate imbibed within a sac involves the use of liposomes to carry enzyme substrates to the area where enzymes are immobilized, presumably at the capture line. Techniques for incorporating substances into liposomes are well known in the art. This technique requires disruption of the liposome at the appropriate time to release the substrate for the enzyme release factor.

Alternatively, an enzyme substrate is encapsulated in a red blood cell (RBC) based on the fact that a RBC can be re-formed after osmotic lysis under the proper conditions of osmolarity, temperature and pH to trap any solutes present at the time of reforming (D'Orazlo et al., *Anal. Chem.*, 49:2083–2086, 1977), hereby incorporated by reference). The resulting loaded erythrocyte ghosts are functionalized with the antigen (or antibody) to an antibody (or antigen) to be quantified. This may be accomplished by mixing the antibody or antigen to be bound to the RBC surface with a suspension of RBCs in the presence of tannic acid, chromium chloride or a water-soluble carbodiimide. The functionalized RBC sacs are then used to carry enzyme substrate to the enzyme at the capture line. Upon capture of the erythrocyte ghost, the hemolysin is brought into close proximity and is able to break down the membrane wall, liberating the enzyme substrate. Also, release can be accomplished by a variety of means, including enzymes, surfactants, ionic strength shifts, complement formation and opsonization. Thus, in FIG. 2, the components are as follows: 24, substrate-loaded erythrocyte ghost; 22, antibody to target analyte on RBC surface; 30, second antibody to analyte; 26, hemolysin conjugated to second antibody.

In both embodiments mentioned above, an enzyme/mediator 26 is immobilized in a mordant within or under the test line 28, or attached to the capture antibody 30. Analyte solution flows from the sample pad 32 to the label pad 34 where the analyte binds to antibody 36. Analyte-antibody conjugate then binds to capture antibody 30 in a sandwich format in the detection zone 38. A suitable enzyme/mediator (release factor) 26 such as Phospholipase C from *C. perfringens* (EC 3.1.4.3) or a surfactant degrades or lyses the particles or sacs 24 to release substrate 22. The sac 24 may be, for example, a liposome prepared by procedures well known in the art, or an erythrocyte ghost as described above. See, for example, U.S. Pat. No. 4,342,826, published PCT Application No. WO80/01515 and U.S. Pat. No. 4,703,017, all of which are hereby incorporated by reference.

Other contemplated release factors include surfactants such as octyl-β-D-glucopyranoside which is stored as a mordant under the capture line as opposed to attached or conjugated to the capture antibody. An alternative system, as described above, is the use of erythrocyte ghosts with enzyme substrates in which hemolysin serves as the enzyme release factor.

When the particle or sac containing the substrate is captured, enzyme substrate leaches from the sac 24 or is released from the particle and enzyme product precipitates on the line or is measured downstream upon enzyme turnover. Unbound antibodies and analyte migrate to the absorbent zone 40.

EXAMPLE 2

Incorporation of Enzyme Substrate within a Biodegradable Sac

To a 500 ml round-bottom rotary evaporator flask was added, with mixing: 240 mg cholesterol, 520 mg distearoyl phosphatidylcholine (20 mg/ml in $CHCl_3$), 18.75 mg distearoyl phosphatidylethanolamine-(p-maleimidophenyl) butyrate (2 mg/ml in $CHCl_3$); 30 mg of isopropyl ether and 5 ml methanol. Subsequently, 25–100 ml of suitable enzyme substrate (2–50 mg/ml in 0.1 M sodium acetate, 0.1 M NaCl, pH 4.5) was added. The mixture was mixed, emulsified by sonication and rotary evaporated at 45–55° C. The warm liposomes were extruded sequentially through 1.0 $\mu$m, 0.7 $\mu$m, 0.5 $\mu$m, then 0.3 $\mu$m, then 0.2 $\mu$m nucleopore polycarbonate membranes. Following a series of high-speed centrifugation (>50,000×g for>30 minutes) and wash steps (0.1 M sodium acetate buffer, 0.1 M NaCl buffer, pH 4.5), liposomes containing entrapped enzyme substrates were resuspended in 10 mM Tris NaCl/EDTA buffer (pH 7.5–8.0 storage buffer) of osmolarity ranging from 200–400 mOs/kg.

Subsequently, anti-human chorionic gonadotropin (hCG) monoclonal antibody was derivatized using the SPDP/DTT procedure. This method involves addition of a pyridyl disulfide group to the anti hCG Mab which is to be added to the surface of the liposome (Wong, S., *CRC Chemistry of Protein Conjugation and Cross-Linking*, CRC Press, Inc., 1991; *Liposomes: A Practical Approach*, R.R.C. New, Ed., IRL Press, 1990, both hereby incorporated by reference.). Briefly, the antibody (about 6 mg/ml) was incubated with a 50-fold molar excess of (N-succinimidyl-3)-[2-pyridyldithio]propionate) (SPDP) previously dissolved in ethanol in 0,1 M sodium phosphate buffer, pH 7.5, for 30 minutes at 25° C. Pyridyl disulfide-labeled antibody was isolated by gel filtration through a Sephadex G-25 column. The pyridyl dithio-Mab solution was titrated in citrate buffer to pH 5.5 by addition of 1 M HCl. a solution of 2.5 m dithiothreitol (DTT, 380 mg/ml) in 0.2 M acetate buffer, pH 5.5 (165 mg sodium acetate/10 ml) was then prepared. To enable formation of a stable thioether bond between the protein and liposome, a 10 $\mu$l aliquot of the freshly prepared DTT solution was added to a mixture of the SPDP-labeled Mab and maleimide-derivatized liposomes at pH 6.5 which was incubated overnight at 25° C.

The method described above resulted in the introduction of 1 to 6 SH groups per antibody as determined by the 5,5' Dithio-(bis(nitrobenzoic acid) (DTNB) method (Deakin et al., *Biochem. J*, 89:296, 1963). In this method, unreacted —SH groups on the protein are blocked with DTNB while unreacted maleimide groups on the liposome are blocked with N-ethyl maleimide. The number of thio groups introduced into the protein is assessed by monitoring the absorbance of free thiopyridone groups at 343 nm that are liberated as the labeling proceeds.

The substrate-loaded liposomes were sensitized on the outer surface by reaction with SH-containing antibody for 2–3 hours at 25° C. Liposomes were then applied to a Sepharose 6FF (Pharmacia) size exclusion column equilibrated in storage buffer containing 2–10 mg/ml BSA, 1.3% glycerol, 0.0005% dimethyl sulfoxide (DMSO), 0.74% EDTA. Liposomes were diluted in storage buffer that was supplemented with a 3:1 mixture of sucrose:trehalose such that the final concentration of lipid in the suspension was between 0.05 to 0.40 $\mu$mole/ml and the final concentration of total sugar was between 5 and 10 mg/ml. This was then lyophilized into either polyester spunlace fabric or nonwoven rayon.

To determine substrate release kinetics from the liposomes in a lateral flow one-step device, the lyophilized materials were cut and assembled as intermediate zones into a device in a manner described in International Publication No. WO92/12428. Capture zone membranes were spotted with anti-hCG polyclonal antibody (1–5 mg/ml) conjugated to the corresponding enzyme or substrate releasing factor. The substrate releasing factor was either phospholipase (1–10 mg/ml), complement component $C_1q$ (0.1–4 mg/ml) or non-ionic polymeric detergents (0.1–0.4%) such as polyoxyethylene alcohols, polyoxyethylene-p-t-octylphenols, polyoxyethylenenonyl phenols, polyoxyethylene sorbitol esters, polyoxypropylene-polyoxyethylene esters of the Triton WR series. Phospholipase may also be attached to the capture antibody directly.

Substrate release from liposomes was studied by applying urine samples with or without hCG to the sample receiving zone and measuring enzyme product accumulation in the capture zone for insoluble products or in the absorbent pad for soluble products. In the case of a colored insoluble product, the optical density was measured using a Umax 6SE flatbed scanner calibrated with a Kodak paper gray scale. In the case of water-soluble products which would precipitate out around the capture line, a densitometer (BioRad Laboratories, Hercules, Calif.) was used which was also calibrated with a Kodak paper gray scale. In both cases, a correlation was observed between gray scale optical density units and analyte concentration that can be used to estimate the analyte level in an unknown specimen.

To assess substrate release from liposomes in a flow-through assay format, the unsupported media containing lyophilized liposomes were cut into 2 cm diameter circles and assembled as a top layer of the device. Capture membranes were prepared similarly as described for the lateral flow device. Substrate release from liposomes was studied by applying urine samples and performing similar measurements as for a lateral flow device.

EXAMPLE 3

Preparation of Biodegradable Substrate-Loaded Particles

Biodegradable synthetic--polyalkylcyanoacrylate (PECA) polymer monosize colloids able to sorb internally sufficient quantities of desirable enzyme substrates were used as carriers for controlled delayed substrate delivery. The general procedure for the polymerization of colloidal particles for sustained drug delivery is described in detail by Cicek et al. (in *Biodegradable Polymeric Biomaterials*, E. Piskin, Ed., Marcel Dekker, N.Y., 1993, hereby incorporated by reference). This procedure was modified to produce particles loaded with an appropriate enzyme substrate in a desired particle size range for either lateral or flow-through assembly and exhibiting adequate degradation kinetics for a particular diagnostic assay format. To this end, the concentrations of the components used in the polymerization process were varied as described herein.

The PECA particles were prepared by polymerization of monomers of 2-ethylcyanoacrylate (ECA) in an acidic aqueous medium containing the desired enzyme substrate. Polymerizations were performed using a copolymer of polyethylene oxide (PEO)/polypropylene oxide (PPO) and a relatively high molecular weight (10,000–50,000) dextran. The dispersion medium consisted of an aqueous solution of hydrochloric acid (HCl) and phosphoric acid ($H_3PO_4$). All components were of analytical reagent grade and PEO/PPO copolymer was identical or similar to that commercially available as F-88 Pluronic Polyol from BASF.

To produce monosize PECA enzyme substrate-loaded particles, the ECA, PEO/PPO dextran, HCl, $H_3PO_4$ and enzyme substrate concentrations were varied between 0.1–12.0% (v/v), 0.2–40 mg/ml, 0.3–100 mg/ml, 0.1–1.5 N, 0.1–15% (v/v), and 0.2–10 mg/ml, respectively. In a typical polymerization process, 1 ml of ECA was added dropwise to 100 ml of vigorously stirred (i.e., ≧1,000 rpm) solution containing PEO/PPO, dextran, phosphoric acid, enzyme substrate and hydrochloric acid, at the concentration ranges indicated above. The sealed vials containing the reaction mixture were stirred at ambient temperature for between 6 and 64 hours and the resultant reaction mixture was processed in a manner conventional for the manufacture of monosize latex particles. Following 2–3 routine washes of the particles with an acidic (<pH 4.0) weak buffer solution, the particles were sized to produce colloids loaded with an enzyme substrate within the desired diameter size. Subsequently, the substrate-loaded PECA particles were diluted in wash buffer to 0.1% to 5% solids. The suspension was poured onto a nonbibulous support, abruptly frozen and lyophilized. Alternatively, the supports containing substrate-loaded particles were air dried overnight in a 45° C. oven or for 24 hours over $P_2O_5$ in vacuo.

To determine substrate release kinetics from the particles in a lateral flow one-step device, the resulting materials were cut into 10×4 mm rectangles and assembled as intermediate zones into a device in a manner described in published PCT Application WO92/12428, which is hereby incorporated by reference. Capture zone membranes were prepared using appropriate enzyme for the particular substrate-loaded PECA particles. Substrate release from PECA particles in buffer solutions of different pH (1.5, 5.0, 6.0, 7.0, 7.4, 8.0, 9.6, 10.5) was studied by applying buffers to the sample receiving zone and measuring color accumulation in the enzyme capture zone for insoluble products or intensity of the color in the absorbent pad for soluble products.

To determine substrate release kinetics from the particles in a flow-through format, the unsupported media containing substrate-loaded PECA particles were cut into 2 cm diameter circles and assembled as a top layer of the device. Substrate release was studied by applying buffer solutions as described above and performing similar measurements as for a lateral flow one-step device. The following observations were made: (1) The substrate-loaded particles obtained with higher amounts of PEO/PPO released substrate faster; (2) Decreasing HCl concentration in the dispersion medium resulted in faster substrate release; and (3) Particles degraded faster, releasing more efficiently with increasing pH of the sample buffer medium.

4. Enzyme product chemical capture

Figure 3:
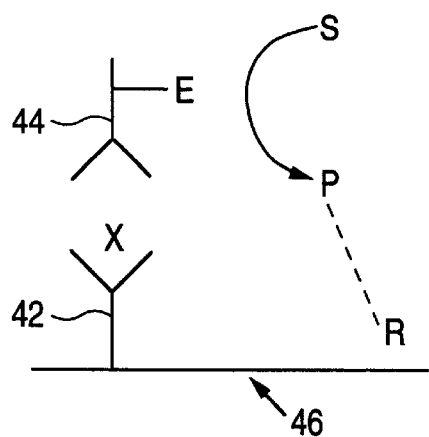
FIG. 3 is a schematic diagram of enzyme product chemical capture. The analyte X is bound by both an enzyme (E)-conjugated antibody and a capture antibody. The enzyme substrate (S) is converted to product (P) which binds to chemical groups (R) immobilized on the support.

In this embodiment, the enzyme product binds specifically to the support which is coated or chemically derivatized with a functional chemical group. Thus, the enzyme product is captured specifically versus simply precipitating at the test line. This technique is schematically diagrammed in FIG. 3. The capture antibody 42 binds to the analyte-antibody-enzyme complex 44 at the test line 46. Enzyme substrate (S) is then converted to product (P) which binds to functional groups (R) at the test line 46 or downstream to form a chemical bond with localization and registration of enzyme by color or other means (i.e., fluorometric, radiolabel, etc.).

EXAMPLE 4

Specific Chemical Capture of Enzyme Product

Compounds capable of reacting specifically with enzyme products were incorporated into the capture zone. For the substrates of alkaline phosphatase, galactosidase or glucuronidase, diazotized amines were incorporated into the capture zone. Examples of such compounds include diazonium salts ("fast salts") and diazotized derivatives of polyamines, or natural polypeptides, such as albumin, immunoglobulins and the like. After enzyme-mediated formation of phenolic products, the diazotized amines react in situ therewith to form stable colored azophenol compounds. Alternatively, the chemical compounds were incorporated downstream from the capture zone [i.e., either in the absorbent pad or in additional intermediate zone(s)] to allow detection of enzyme products away from the capture zone.

5. Delay zone dissolution for delivery of substrate and/or conjugate

This lateral flow embodiment uses separate paths that employ time-delayed dissolution of barrier zones for delivery of substrate and/or conjugate reagents to the test area. This facilitates early release and migration of antibody enzyme label (as conjugate), which facilitates delayed release of substrate for catalysis. Barrier 1 dissolves first to release enzyme-antibody conjugate, while barrier 2 dissolves later to release substrate. The enzyme product precipitates at the test line or is measured downstream.

EXAMPLE 5

Delayed enzyme substrate delivery using hydrogel barrier zones

Figure 4:
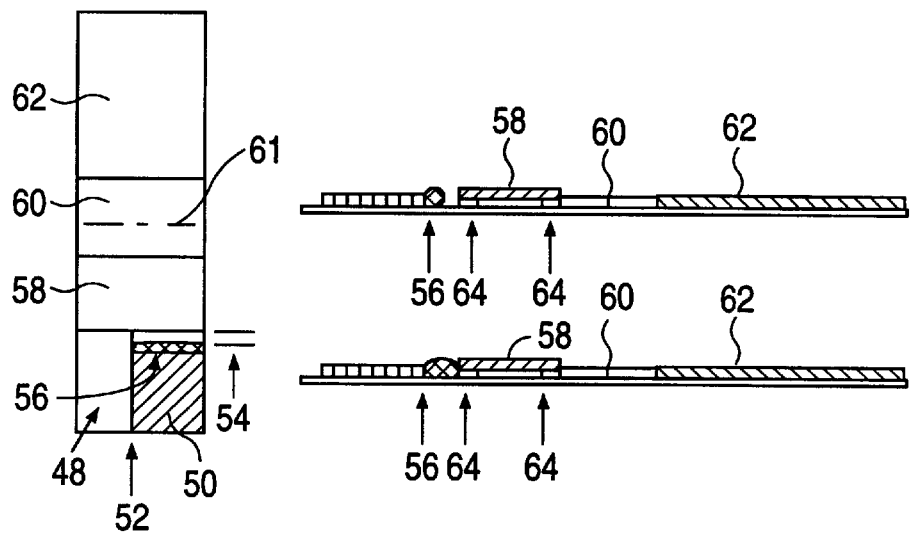
FIG. 4 is a schematic diagram of an enzyme immunoassay test strip for delayed enzyme substrate delivery using hydrogel barrier zones.

Referring to FIG. 4, to construct delayed enzyme substrate delivery using structural hydrogel barrier zones, the desired enzyme substrate for the corresponding enzyme was dissolved in the pH activity optimum buffer at 0.2–3 mg/ml and supplemented with 10 mg/ml BSA prepared in the same buffer. The enzyme substrate mixture was then lyophilized in a nonbibulous support 50 such as polyester or polyacrylic spunlace fabric. A printed hydrophobic polyurethane barrier line 52 separates nonbibulous support 48 (no substrate) from nonbibulous support 50 (containing substrate). The enzyme-antibody label pad 58 was prepared by pouring the enzyme-antibody conjugate (5–50 µg/ml) supplemented with the appropriate activators and stabilizers onto a similar support followed by lyophilization. Capture zone nitrocellulose membranes 50 were spotted with anti-hCG polyclonal antibody at 1 to 5 mg/ml and blocked with 10 mg/ml BSA or 0.2–2% (w/v) polyvinyl alcohol. Fluid communication bridges 64 permit fluid flow between the sample pad-label pad and label pad-capture zone.

In order to determine delayed enzyme substrate delivery in a lateral flow "one-step" device, the materials described above were cut and assembled as consecutive intermediate zones into a device except that a 3–10 mm gap 54 was created between enzyme substrate pad 50 and enzyme-antibody label pad 58. Subsequently, a strip of Hypan TAU92 (Taupan) molecular hydrogel sponge was laid down against the edge of the enzyme substrate pad, leaving a gap between the enzyme-antibody label pad.

Structural (molecular) hydrogel barrier sponges 56 were constructed using Hypan polymers (Hymedix International, Inc., Dayton, N.J.) which are hydrophilic acrylate derivatives with multi-block copolymer structures of several sequences of amorphous units with pendant hydrophilic groups derived from acrylic acid (soft blocks) responsible for swelling (flexibility) and several sequences of organized, crystalline pendant polyacrylonitrile structures (hard blocks) responsible for mechanical properties. Particularly preferred polymers are highly swelling associative polymers known as Hypan TN (Transient Network) Hydrogels, whose hard blocks form reversible meltable transient clusters. Subsequently, substrate release was studied by simultaneously applying urine or serum samples with or without various levels of hCG to zones 48 and 50 of a sample pad divided by a barrier zone 52 and measuring enzyme product accumulation in the capture zone 60 for insoluble products or in the absorbent pad 62 for soluble products.

Figure 5:
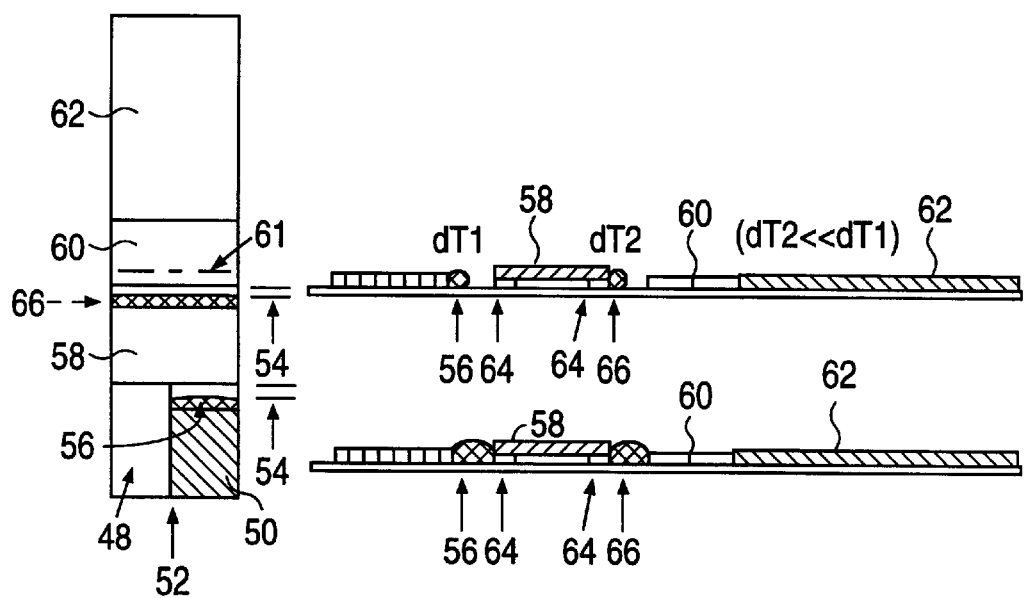
FIG. 5 is a schematic diagram of an enzyme immunoassay test strip for sequential delayed enzyme-antibody and enzyme substrate release using hydrogel barrier zones.

As shown in FIG. 5, sample is added concurrently to both zones 48 and 50 of a sample-pad that has been divided by a barrier zone 52 that has been printed onto Sontara spunlace fabric. Zone 50 is loaded with enzyme substrate that has been lyophilized. Due to hydrophobic barrier 52, half of the sample volume sits in zone 50 until the hydrogel barrier zone 56 imbibes enough fluid to expand and close the gap 54 separating zone 50 from the label pad 58. Meanwhile, the fluid in zone 48 has made progress forward such that the enzyme-antibody label has been picked up and the immune complex formed at the capture line 61 within the nitrocellulose membrane 60. At a later time, the substrate picked up in zone 50 arrives at the capture line 61 which now has immobilized antibody associated therewith. The delay imposed by the expansion time required by Hypan to close the gap has allowed time for bound/free separation of uncomplexed antibody and analyte to occur before arrival of the substrate.

EXAMPLE 6

Sequential Delayed Enzyme-Antibody and Enzyme Substrate Release Using Hydrogel Barrier Zones Referring to FIG. 5, in a variation of Example 5, a 3–10 mm gap 54 was also created between the enzyme-antibody zone 58 and the capture zone 60, and a strip of Hypan sponge 66 was laid down against the edge of the enzyme-antibody label pad 58, leaving a gap 54 between the capture zone 60 and the label pad 58. To achieve sequential delayed release of enzyme-antibody label after initial incubation with the sample (to increase immunological efficiency), followed by delayed enzyme substrate release from the enzyme substrate zone, different widths of sponge were used to facilitate desired swelling time.

The performance of the device was tested by simultaneously applying urine or serum samples without or with various levels of hCG to the enzyme substrate zone 50 and the enzyme-antibody label zone 58, and measuring enzyme product accumulation in the capture zone 60 for insoluble enzyme products or in the absorbent pad 62 for soluble products.

The Hypan sponge 66 increases the dwell time of the sample analyte within the label pad 58 to promote increased immunological efficiency. As sponge 66 swells, it closes the gap between the label pad 58 and capture zone 60, permitting fluid communication between these sections. Hypan sponge 56 closes somewhat later such that delivery of the enzyme substrate occurs after bound/free separation of surplus enzyme conjugate is essentially complete.

EXAMPLE 7

Sequential Delayed Enzyme-Antibody and Enzyme Substrate Release Using Enterosoluble Coating Barrier Zones In a variation of the example just described, the enterosoluble methacrylic acid copolymer coatings similar to those used for solid pharmaceutical dosage (Eudragit S100; Rohm Tech., Inc., Malden, Mass.) were used to achieve sequential release of enzyme-antibody label followed by enzyme substrate. For example, to achieve sequential delayed release of alkaline phosphatase (ALP)-labeled anti-hCG monoclonal antibody conjugate followed by the ALP substrate, the conjugate (0.5–10 μg/ml) was prepared in 50 mM Tris-HCl buffer (pH 8.5) containing 5 mg/ml BSA, 1 mM $MgCl_2$ and 0.1 mM $ZnSO_4$, then lyophilized into a nonbibulous support as described above. The desired ALP substrate (i.e., 3-indoxylphosphate) was dissolved at 0.4–3 mg/ml in 0.1 M 2-amino-2-methyl-1-propanol (AMP) buffer (pH 10.5) and lyophilized into a nonbibulous support as described above. Capture zone membranes were spotted with anti-hCG monoclonal antibody at 1–5 mg/ml and blocked with 10 mg/ml BSA or 0.2–2% (w/v) polyvinyl alcohol.

Figure 6:
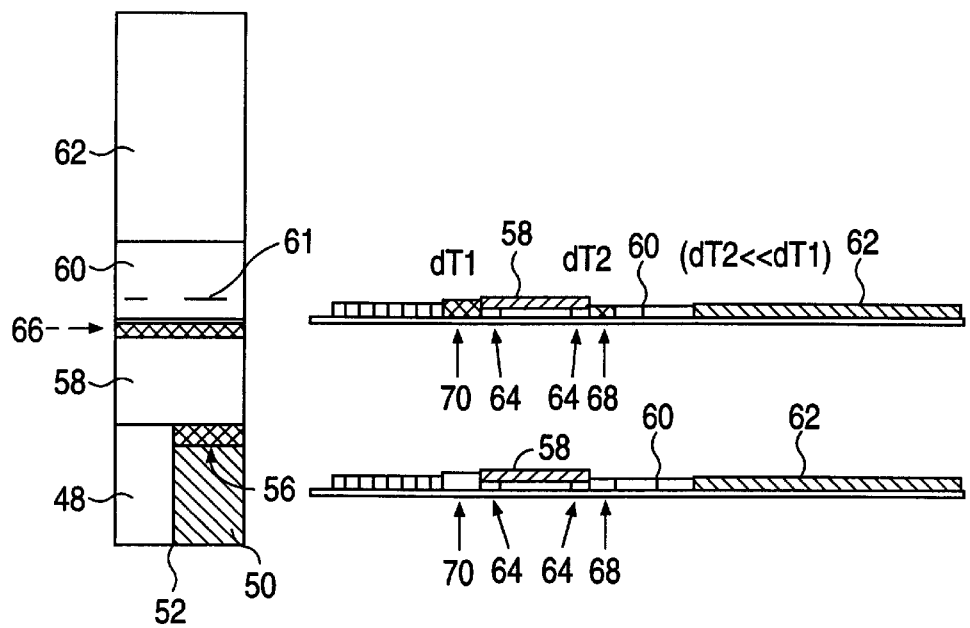
FIG. 6 is a schematic diagram of an enzyme immunoassay test strip for sequential delayed enzyme-antibody and enzyme substrate release using enterosoluble barrier zones.

Subsequently, the materials were cut and assembled as consecutive intermediate zones into a lateral flow one-step device as shown in FIG. 6, except that 2–5 mm gaps were created between the ALP substrate pad and the ALP-monoclonal antibody label pad, as well as between the label pad and capture zone. In order to create the desired barrier zones, two anionic copolymer mixtures based on methacrylic acid (MAA) and methylmethacrylate (MMA) were prepared in methanol at 3–15% (w/v). Copolymer A comprised a MAA to MMA ratio of 12:88 and Copolymer B comprised a MAA to MMA ratio of 3:97. Copolymers A and B were dried separately in nonbibulous supports 68 and 70, respectively. Subsequently, the gap between the ALP substrate pad and the ALP-monoclonal antibody (MAb) label pad (see FIG. 5) was closed by attaching--rectangles of support 70 containing Copolymer B with a 1 mm overlap on both sides. Similarly, the gap between the label pad and capture zone (see FIG. 5) was closed using support 68 containing Copolymer A.

Copolymer B, having the lower ratio of MAA to MMA, will dissolve more slowly than copolymer A and will enable delivery of the enzyme substrate to the capture zone later than enzyme-antibody conjugate. Due to the generally high pH (8–9.5) required by the ALP enzyme reaction, the methacrylic acid units in the copolymer ionize to bring about breakdown and dissolution of the copolymer. Copolymer A, with its higher mole % MAA, dissolves relatively quickly, allowing earlier delivery of enzyme-antibody conjugate to the capture line, but increases the dwell time of the analyte within the label pad sufficiently to enhance immunological efficiency.

Performance of the device was assessed by simultaneously applying urine samples, with or without hCG, to the ALP substrate pad and ALP-MAb label pad and performing similar measurements as described above.

EXAMPLE 8

Sequential Delayed Release of Enzyme-Antibody Label and Enzyme Substrate Using Biodegradable Phospholipid Barrier Zones In a variation of Example 7, biodegradable phospholipid barriers were used to achieve sequential release of antibody-enzyme label followed by enzyme substrate in the lateral flow one-step device. ALP-MAb label pad and ALP substrate pad were prepared as described in Example 7, except that the nonbibulous supports were supplemented with various amounts of phospholipase (1–20 µg/ml), with the concentration in the substrate pad lower than that in the label pad to allow dissolution of the enzyme-antibody barrier zone prior to dissolution of the substrate barrier zone. Subsequently, the pads and capture zone were assembled into a lateral flow one-step device with 2–5 mm gaps left between the substrate and label pad, as well as between the label pad and capture zone. To create the desired barrier zones, liposomes were prepared as described in Example 2 except that enzyme substrate was not included and liposomes were not extruded through the membranes. Liposomes were dried in a nonbibulous support and gaps were closed using the liposome support.

Performance of the device was assessed by simultaneously applying urine samples (with or without hCG) to the ALP substrate pad and ALP-MAb label pad, and performing similar measurements as described in the previous example.

6. Delayed release of enzyme substrate using protected enzyme substrate

This embodiment encompasses multi-enzyme systems wherein the time-dependent production of the end product of the first enzyme reaction is the substrate for the enzyme-antibody conjugate reaction. Referring to EIA device 72 shown in FIG. 7, substrate (S1) for the first enzyme (E1) is immobilized in excess in a sample pad 74. After immunological separation upon lateral flow of a solution containing an analyte (X), the time-dependent catalysis of the substrate for the enzyme-antibody complex (E2-Ab2) begins with E1 acting on S1 to produce substrate 2 (S2) in label pad 76. When the concentration of S2 reaches an effective threshold concentration for E2 to become active, the product (P) begins to form in the capture zone 78. By this time, sufficient delay has occurred so that most or all of the target analyte has been recognized and captured at the test line 80. The product (P) is then directly quantified by absorbance as a colored product, electrochemically as an electroactive substance, fluorometrically, luminescently or is free to participate in a secondary chemical reaction so as to make possible one of these modalities of detection either as a captured material or measured downstream as a soluble material. Unbound analyte and antibodies flow to absorbent zone 82. A specific example of this EIA is described in Example 9.

EXAMPLE 9

Figure 7:
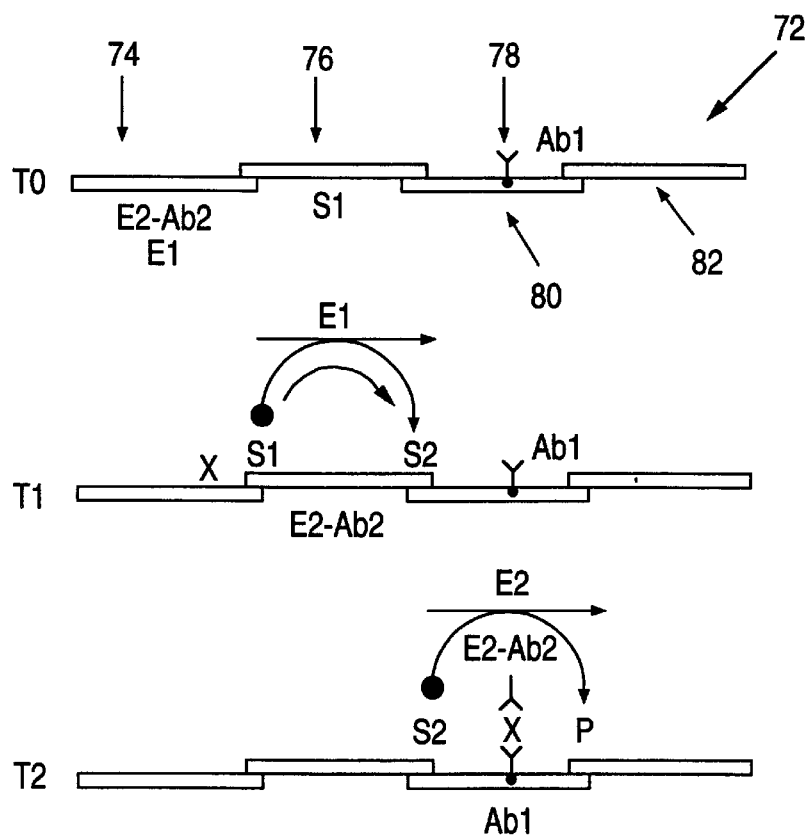
FIG. 7 is a schematic diagram of delayed release of enzyme substrate using multi-enzyme systems and protected enzyme substrates. X=analyte; $E_1$=enzyme 1; $E_2$=enzyme 2; S=substrate; P=product.

In this example, referring to FIG. 7, E2-Ab2=β-D-galactosidase-anti-hCG; E1=ALP; S1=o-nitrophenyl-β-D-galactopyranoside-6-phosphate; S2=o-nitrophenyl-β-D-galactopyranoside; Ab1=goat-anti-hCG; P=o-nitrophenol. The conjugate of $E.\ coli$ β-D-galactosidase and an anti-hCG MAb was prepared in 50 mM HEPES, pH 7.5 containing 1 mM $MgCl_2$ and diluted to 0.5–10 µg/ml in the same buffer supplemented with 5 mg/ml BSA (the conjugate diluent). ALP was added to the conjugate solution to a final concentration of 10 µg/ml to 1 mg/ml, and the final mixture was lyophilized into a nonbibulous support as described above (the sample pad). O-nitrophenyl-β-D-galactopyranoside-6-phosphate cyclohexylammonium salt (S1) (Sigma) was dissolved at 0.1–1.5 mg/ml in the conjugate diluent and lyophilized into a nonbibulous support as described above (the label pad). The capture zone was prepared as previously described. Subsequently, the just-described materials were cut and assembled as consecutive intermediate zones into a lateral flow one-step device.

Figure 8:
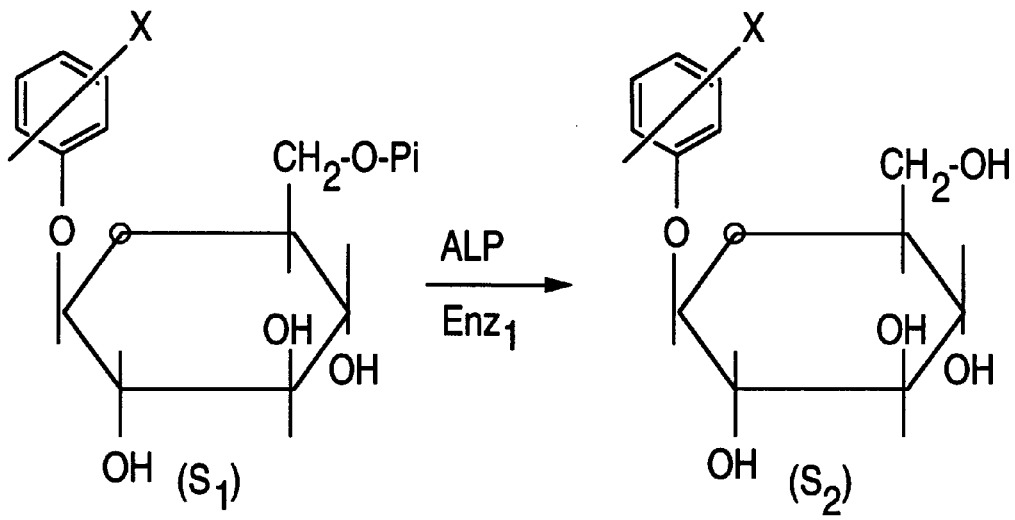
FIG. 8 is a schematic diagram of delayed release of enzyme substrate using the β-D-galactosidase anti-analyte system.
Figure 8:
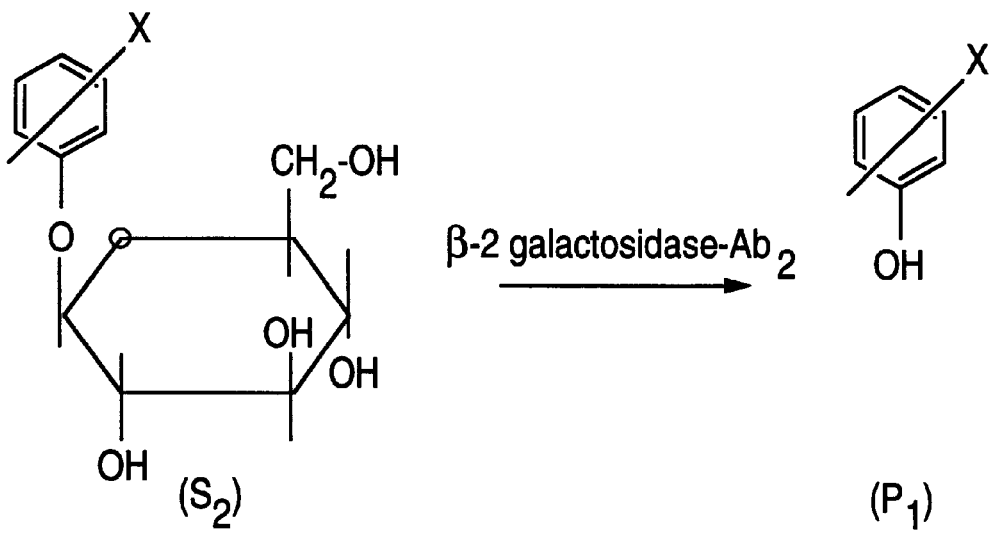

Performance of the device and delayed release of enzyme substrate was assessed by applying urine samples (with or without hCG) to the label pad and performing similar measurements as previously described for a lateral flow one-step device. The reaction scheme is summarized in FIG. 8 in which S1=O-nitrophenyl-βD-galactopyranoside-6-phosphate; S2=O-nitroophenyl-β-D-galactopyranoside and P1=O-nitrophenol. The product was measured colorimetrically by absorbance.

Figure 9:
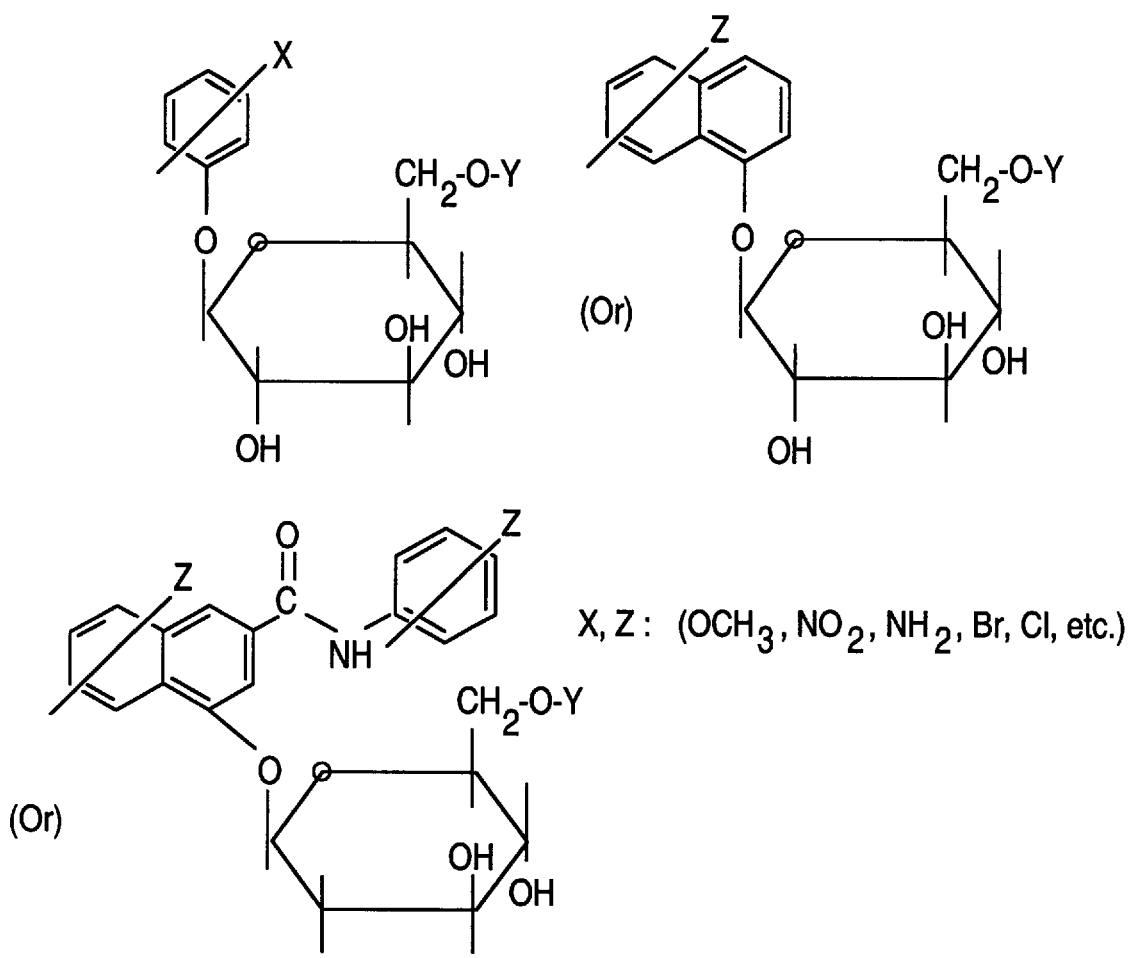
FIG. 9 shows alternative "protected" substrates for the β-D-galactosidase-Ab conjugate shown in FIG. 8.

Alternative "protected" substrates for the β-D-galactosidase-E2 conjugate and corresponding enzymes E1 are shown in FIG. 9. Table 2 shows alternative "protected" substrates for the E2-Ab conjugate when the β-D-galactose substrate core is replaced with other sugars, as well as the corresponding enzymes E2. FIG. 10 shows "protected" substrates for urease as E1 in the E1-Ab conjugate.

In each case in Table 2 below, the sugar group in the left column would be protected by the presence of a phosphate group or other protecting group as indicated in FIG. 9. The nitrophenyl, bromophenyl, chlorophenyl, methoxyphenyl or aminophenyl groups are removed by the corresponding enzyme in the right column and the product quantified by the appropriate modality.

TABLE 2

| Substitute for β-D-galactase | $Enz_2$ |
|---|---|
| 2-acetamido-2-deoxy-β-D-glucosaminide | N-acetyl glucosaminidase (EC 3.2.1.52) |
| α-L-arabinofuranose | α-L-arabinofuranosidase III |
| β-D-cellobiose | exglucanase |
| N,N'-diacetyl-β-D-chitobiose | chitobiosidase |
| α-L-fucopyranose | α-L-fucosidase (EC 3.2.1.51) |
| β-D-fucopyranose | β-D-glycosidase |
| α-D-galactose | α-galactosidase (EC 3.2.1.23) |
| β-D-glucose | β-glucosidase (EC 3.2.1.21) |
| α-D-glucose | glucansucrase |
| β-D-glucopyranosiduronic acid | β-D-glucoronidase |
| α-D-maltoheptose | α-amylase (EC 3.2.1.1) |
| α-D-maltohexose | α-amylase |
| (α or β)-mannopyranose | (α or β)-mannosidase |

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A lateral flow enzyme immunoassay device, comprising:
    a sample pad comprising a first lane and a second lane separated by a hydrophobic barrier, wherein said first lane contains an enzyme substrate and said second lane contains an enzyme-antibody conjugate having affinity for an analyte;
    a capture zone separate from said sample pad, which is in fluid communication with said first lane and said second lane of said sample pad prior to initial application of a sample, said capture zone having a capture antibody incorporated therein having affinity for said analyte; and
    an absorbent zone in fluid communication with said capture zone;
    wherein said second lane transports a fluid at a faster rate than said first lane.

2. The immunoassay device of claim 1, wherein said analyte is selected from the group consisting of hormones, enzymes, lipoproteins, bacterial or viral antigens, immunoglobulins, lymphokines, cytokines, drugs and soluble cancer antigens.

3. The immunoassay device of claim 1, wherein said sample pad comprises high density polyethylene.

* * * * *